US00PP10503P

United States Patent [19]

de Ridder

[11] Patent Number: Plant 10,503

[45] Date of Patent: Jul. 14, 1998

[54] BEGONIA PLANT NAMED 'PINTO'

[75] Inventor: Geert J. W. de Ridder, Aalsmeer, Netherlands

[73] Assignee: Begonia Breeders Assoc. B.V., Aalsmeer, Netherlands

[21] Appl. No.: 811,737

[22] Filed: Mar. 6, 1997

[51] Int. Cl.[6] ..... A01H 5/00

[52] U.S. Cl. ..... Plt./87.18

[58] Field of Search ..... Plt./87.17, 87.18

*Primary Examiner*—James R. Feyrer

*Attorney, Agent, or Firm*—C. A. Whealy

[57] ABSTRACT

A distinct cultivar of Begonia plant named 'Pinto', characterized by its large, attractive light pink fully double flowers that are about 8.5 cm in diameter; resistance to powdery mildew under commercial greenhouse conditions; and excellent postproduction longevity.

1 Drawing Sheet

1

The present invention relates to a new and distinct cultivar of Begonia plant, botanically known as *Begonia×hiemalis*, commerically known as Elatior Begonia, and referred to by the cultivar name 'Pinto.'

The new cultivar was discovered by the inventor in a controlled environment in Amstelveen, The Netherlands, in 1994, as a mutation of the nonpatented Elatior Begonia cultivar Schwabenland. The new cultivar was observed as a single plant in a group of 13-cm flowering plants of the parent cultivar. The selection of this plant was based on its light pink flower color, fully double flower form and resistance to powdery mildew. A detailed comparison of plants of the new Begonia and the cultivar Schwabenland appears in Chart A at the end of the specification.

Asexual reproduction of the new cultivar by terminal cuttings taken in a controlled environment in Aalsmeer, The Netherlands, has shown that the unique features of this new Begonia are stable and reproduced true to type in successive generations.

The cultivar 'Pinto' has not been observed under all possible environmental conditions. The phenotype may vary somewhat with variations in environment such as temperature, daylength and light intensity, without, however, any variance in genotype. The following traits have been repeatedly observed and are determined to be the unique characteristics of 'Pinto'. These characteristics in combination distinguish 'Pinto' as a new and distinct cultivar:

1. Large and attractive light pink fully double flowers that are about 8.5 cm in diameter.

2. Resistance to powdery mildew under commerical greenhouse conditions.

3. Excellent postproduction logevity.

The accompany colored photograph illustrates the overall appearance of the new cultivar, showing the colors as true as it is reasonably possible to obtain in colored reproductions of this type. The photograph comprises a top perspective view of a typical flowering plant of 'Pinto'. Flower and foliage colors in the photographs may differ from the actual colors due to light reflectance.

In the following description, color references are made to The Royal Horticultural Society Colour Chart except where general terms of ordinary dictionary significance are used. The following observations and measurements describe plants grown in Aalsmeer, The Netherlands, that were flowered in November under commerical practice in a glass-covered greenhouse. Average day temperatures were 20° C. and average night temperatures were 18° C. Assimilation lights provided a maximum light level of 18,000 lux. Measurements and numerical values represent averages for six typical flowering plants.

2

Botanical classification: *Begonia×hiemalis* cultivar Pinto.

Commercial classification: Elatior Begonia.

Parentage: Naturally-occuring mutation of single-flowered *Begonia×hiemalis* cultivar Schwabenland.

Propagation:

*Type.*—Terminal cuttings.

*Time to rooting.*—About 14 days with soil temperatures of 23° C.

*Rooting habit.*—Fine, fibrous and well-branched.

Plant Description:

*Plant form.*—Upright and rounded potted plant, freely branching with good stem and stem base strength. Flowers are fully double and abundant. Plants flower continuously.

*Growth habit.*—Moderate growth rate and moderately vigorous. Suitable for 10 to 15-cm containers. Under optimal environmental and cultural conditions, usually 10 weeks are required to produce proportional 13-cm potted plants from terminal cuttings. Vegetative shoots are formed at basal nodes and flowering shoots are formed at upper modes.

*Plant height.*—About 30 cm.

*Plant width.*—About 25 cm.

*Leaves.*—Arrangement: Simple, alternate. Size: Length: About 27 cm. Width: About 19 cm. Shape: Asymmetrically cordate. Apex: Acute. Base: Cordate, overlapping. Margin: Undulating and lacerate. Texture: Smooth and leathery. Color: Young foliage: Upper surface: 143A. Lower sufrace: 138B. Mature foliage: Upper surface: 139A. Lower surface: 138B. Venation: Upper surface: Light green. Lower sutface: 138B.

Flower description:

*Flowering habit.*—Fully double and large flowers arranged in racemes. Many racemes in flower simultaneously. Flowering continuous.

*Natural flowering season.*—Plants will flower year around regardless of daylength, however plants will flower earlier and more abundantly if daylength is 12 hours or less. Usually plants start flowering after 7 weeks of start of short day/long night treatments.

*Flowers.13* Shape: Flattened, oval. Diameter: About 8.5 cm.

*Tepals.*—Arrangement: Rosette. Shape: Rounded with undulating margin. Quantity per flower: Usually about 24 per flower. Color: When opening: 49B/52D. Fully opened: Upper surface: 49B/52D. Lower surface: 49B. Texture: Smooth, velvety, glabrous.

*Sepals.*—Arrangement: Two, opposite. Shape: Oval. Color: 144C.

*Reproductive organs.*—Stamens: None. Pistils: None.

Postproduction longevity:

*Individual flowers.*—Generally 3 weeks.

*Whole plants.*—About 6 weeks under interior conditions.

Disease resistance: Plants of the cultivar 'Pinto' are resistant to Powdery Mildew under greenhouse conditions.

Seed production: Seed production has not been observed as reproductive organs are not formed.

CHART A

| CHARACTERISTIC | 'PINTO' | 'SCHWABENLAND' |
|---|---|---|
| LEAF LENGTH | About 27 cm | About 22 cm |
| LEAF WIDTH | About 19 cm | About 15 cm |
| LEAF MARGIN | Undulate and lacerate | Serrate |
| LEAF COLOR, YOUNG, UPPER SURFACE | 143A | 141B |

-continued

CHART A

| CHARACTERISTIC | 'PINTO' | 'SCHWABENLAND' |
|---|---|---|
| LEAF COLOR, MATURE, UPPER SURFACE | 139A | 141A |
| FLOWER FORM | Double | Single |
| NUMBER OF TEPALS | About 24 per flower | 4 per flower |
| TEPAL MARGIN | Undulate | Flat, entire |
| TEPAL COLOR, WHEN OPENING | 49B | 43A |
| TEPAL COLOR FULLY OPENED, UPPER SURFACE | 49B | 43A |
| TEPAL COLOR, FULLY OPENED, LOWER SURFACE | 49B | 44A |
| DISEASE RESISTANCE | Resistant to Powdery Mildew | Susceptible to Powdery Mildew |

It is claimed:

1. A new and distinct cultivar of Begonia plant named 'Pinto', as illustrated and described.

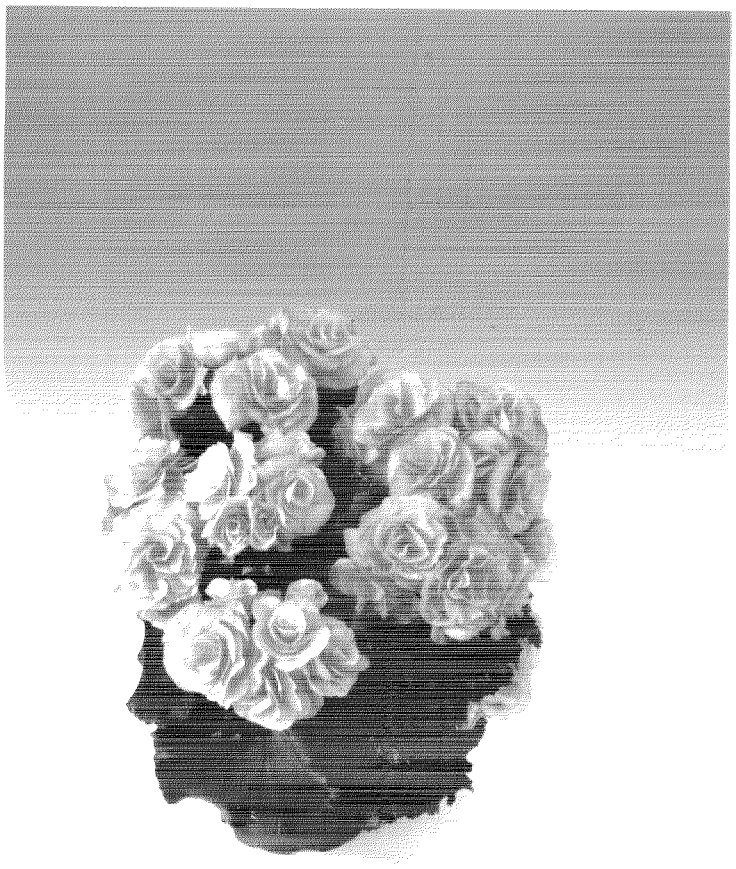

* * * * *